United States Patent [19]

Pfleger

[11] Patent Number: 5,236,420
[45] Date of Patent: Aug. 17, 1993

[54] BYPASS, PRESSURISING PISTION FOR CHAMBERS

[76] Inventor: Frederick W. Pfleger, 1152 Barbara Dr., Cherry Hill, N.J. 08003

[21] Appl. No.: 890,772

[22] Filed: Jun. 1, 1992

[51] Int. Cl.⁵ ............... A61M 1/00; A61M 5/315
[52] U.S. Cl. .................. 604/122; 604/219; 604/220; 604/222
[58] Field of Search ............ 604/56, 82, 89-91, 604/122, 187, 218-222, 236-238, 247, 249, 140-141, 124, 125, 228

[56] References Cited

U.S. PATENT DOCUMENTS

| | | | |
|---|---|---|---|
| 3,147,753 | 9/1964 | Nogier et al. | 604/222 |
| 3,678,931 | 7/1972 | Cohen | 604/90 |
| 4,266,557 | 5/1981 | Merry | 604/222 |
| 4,299,238 | 11/1981 | Baidwan et al. | 604/122 |

*Primary Examiner*—Randall L. Green
*Assistant Examiner*—P. Zuttarell

[57] ABSTRACT

A resilient material pressurizing plunger for syringes or like containers in which the plunger construction is such that on the initial insertion into the syringe by a first inserting member, the plunger is distortable thus allowing the gas pressure generated by the plunger insertion to escape. The plunger is also capable of pressurizing the chamber when further insertion occurs by use of a second insertion member which prevents the distortion.

15 Claims, 1 Drawing Sheet

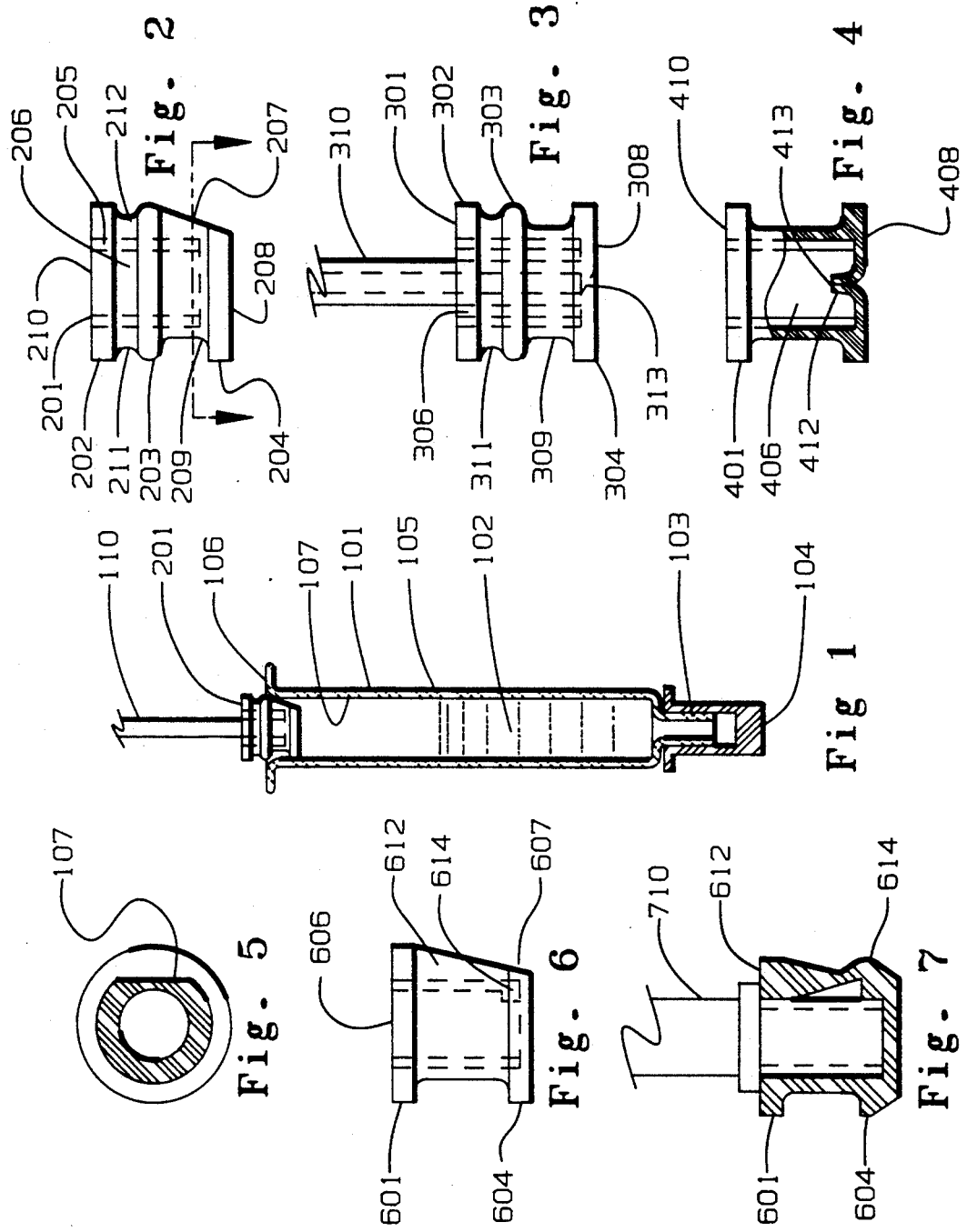

BYPASS, PRESSURISING PISTION FOR CHAMBERS

BACKGROUND OF THE INVENTION

As is well known in the art, when a resilient material plunger is inserted into a closed chamber, the movement of the plunger from the open end of the chamber into the chamber compresses the air or gas that is ahead of the plunger. The greater the amount of movement the greater the amount of pressure build up. As a result this insertion pressure, plus additional pressure due to temperature buildup, plus any reduction in pressure behind the piston will cause the piston to move back out from the chamber. Many techniques are used to prevent this from occurring. These include use of a bleed wire alongside the piston which allows the pressurized gas or air to escape alongside the bleed wire, inserting the piston through a tube which fits inside the opening of the chamber thus allowing the pressurized gas or air to flow past the tube since the tube is not a sealing member, or the plunger can be inserted into the chamber after the chamber has been evacuated in a vacuum chamber. Although all of these techniques work, they are expensive, they slow down production, and in sterile operations these techniques introduce other factors which can easily effect sterility. In my patent U.S. Pat. No. 4,929,230 is disclosed a plunger design which under certain conditions allows material to flow past the plunger. This invention changes the design of the plunger of the above mentioned patent to achieve the desired results of having the plunger bypass gas or air pressure under one condition of operation and still is capable of providing pressure on the contents of the chamber or provide pressure on the contents to eject the contents from the chamber.

SUMMARY OF THE INVENTION

Among the objects of this invention is to provide a chamber plunger which within itself it can allow the gases or air in the chamber to escape during the positioning of the plunger and still allow the plunger to act in a normal fashion during normal functioning of the plunger.

It is a more particular object of this present invention to provide a chamber plunger which can achieve the desired results and can still be fabricated at a cost just about equal to the coast or existing designed plungers.

It is a more particular object of the present invention to provide a chamber plunger which can provide the desired results for any size chamber.

It is a more particular object of the present invention to provide a chamber plunger which can utilize the standard plunger rods in existence for pressurizing the chamber.

Other objects of the present invention will become apparent upon reading the following specification and referring to the accompanying drawings which form a material part of this disclosure.

BRIEF DESCRIPTION OF THE DRAWINGS

FIG. 1 is a cross section of a syringe with the piston at the first stage of entering the syringe.

FIG. 2 is across section of a plunger showing one portion of the periphery tapered to generate a collapsible surface which will provide an air path when the wall is collapsed.

FIG. 3 is a cross section of a plunger showing the bottom surface of the plunger with a slit which is openable to form an air path.

FIG. 4 is a cross section of a plunger showing the bottom surface shaped into the form of a duckbill which is openable to form an air path.

FIG. 5 in a plan view of a plunger that has a portion of it's wall collapsible.

FIG. 6 is a cross section of the plunger with an insertion rod installed and with a buildup on the inner end.

FIG. 7 is a cross section of a plunger with a pressurized rod installed showing the rib expanded on the outer surface.

DESCRIPTION OF PREFERRED EMBODIMENT

Referring now more particularly to the drawings specifically to FIGS. 1-7, there is shown various configurations of a resilient material piston that can function as a bypass piston for syringes or like type chambers or it can function as a pressurizing piston for syringes or like chambers. In this description the term syringes will be used to encompass all such chambers. The word gas will be used to include air or fluids. The piston in the bypass mode allows gas to pass in one direction and in the pressurizing mode the piston either pressurizes the chamber contents or pressurizes the chamber to expel the contents from the chamber. As shown in FIG. 1, a syringe 101 is provided at one end with a necked down portion 103, through which the contents, generally fluids, exit. This necked down end is either provided with an injection needle or a sealing cover 104. If a needle is used, it also is provided with a sealing cover. The sealing cover 104 on the syringe or the needle is used to prevent the contents from exiting during filling, during plunger insertion or while not in use. The syringe body 105 is used to hold the contents 102. The open end 106 of the syringe 101 enables easy inserting of the contents 102 to the specified amount and for accepting the piston. After the contents 102 are inserted, the piston 201 is inserted into the opening. Since the resilient material of the piston 201 is a close fit or a compressible fit with the inside 107 of the syringe body 105, gas inside the barrel is compressed as the piston 201 is inserted. This compressed gas will prevent seating the piston 201 at the desired depth. Even though the piston is moved into the syringe body 105 the desired amount, the built up gas due to the fit between the piston and the inside 107 will push the piston outward. If the internal gas pressure is also raised due to temperature increases, the piston will be moved outward even further. If the external air pressure is reduced as would occur if the part is subjected to a high altitude environment, the gas pressure inside the syringe will also move the piston outward further until the internal and external pressures are balanced. In order to prevent this gas pressure build up as the piston 201 is inserted into the syringe 101, bleed wires, bleed strips, or hollow tubes are placed alongside the piston 201 to allow the pressurized gas to escape through a channel that is generated between the resilient material of the piston 201 and the inner wall 107 of the syringe 101. Another technique that is used is to place the syringe 101 with the contents 102 into a vacuum chamber. The chamber is then evacuated which removes the air from the syringe 101. The piston 201 is then inserted into the open end 106 and since the gas has been removed there is no internal pressure buildup. As a result, both of these methods allow for the seating of the piston 201 at the desired position since the internal pressure and the external pressure are substantially balanced. Even though these methods produce the desired results they are very costly, they limit production speeds and they can provide for cross contamination of the materials placed in the syringes.

As shown in FIG. 2 a first configuration of a piston that will produce the desired results is shown. The piston 201 is provided with an inner end 208 and outer end 210. The terms inner end and outer end used here represents the portions of the piston as they go into the syringe. The outer end 210 in FIG. 2 consists of the two sealing rings 202 and 203 and the relief ring 211. The inner end 208 consists of a partial surface 204 and a relief ring 209. Between the portions of the sealing surface 204 that has been removed and the sealing ring 203 is a tapered connecting outer surface 207. Although shown as one surface, there may be many such surfaces around the piston or the entire partial sealing surface can be removed resulting in a tapered surface 207 extending around the piston. Between the inner end 208 and the outer end 210 is the resilient material connecting wall 212. The outside of the resilient material connecting wall 212 consists of the sealing sections 202 and 203, the relief ring 211 and the tapered surface 207. It is obvious that the sealing sections 202 and 203 and the relief ring 211 can be combined to provide a single sealing ring as shown in FIGS. 4,6,7. The inside of the connecting wall 212 can be a plain surface or it can be a threaded surface that mates with a threaded actuating member to be described later. The inside of the connecting wall 212 therefore forms a cavity 206 in the piston 201. The bottom of the cavity being the inner end 208.

When the piston 201 is inserted in the syringe 101 FIG. 1 by means of a first actuating member 110 pushing on the inner end 208, the tapered outer surface 207 enters the syringe inner surface 107 first. When the sealing rings 202 and 203 enter the syringe 101 the sealing rings seal against the inner wall 107. Standard pistons in use today prevent any gas in the syringe from escaping as the piston is compressing the gas as it is inserting except as previously described. When the gas pressure which acts on the tapered outer surface 207 reaches the predetermined pressure that will collapse the connecting wall 212, the connecting wall 212 will collapse inwardly into the cavity 206. This function is similar to that which is fully described in my patent U.S. Pat. No. 4,929,230. The actuating member 110 which is moving the piston 201 into syringe 101 is smaller than the cavity 201, as a result the connecting wall 212 has room to collapse. When connecting wall 212 collapses, it forms a passageway between the syringe wall 107 and the piston 201 through which any gas under pressure can escape through the passageway until the inside pressure is relieved to approximate the outside pressure. This relieving of inside gas pressure will continue until the piston 201 is moved up to and into contact with the contents 102. Further insertion would apply pressure to liquid contents and would also let the liquid bypass the piston out of the syringe. This technique could be used in applications to insure a uniform fill in syringes by first overfilling and then removing the excess by the manner just described.

Other forms of piston that also could produce these features are shown in FIG. 3 and FIG. 4. In FIG. 3, the inner surface 408 is provided with a self sealing slit 313. In FIG. 4, the inner surface 408 is provided with a slit 413 at the top edge of two duckbill flaps 412. The slits 313 and 413 are designed to open at a given pressure, generally a very low pressure. The design of the slit opening pressure is similar to the wall collapsing pressure as previously described. When the piston 301 or 401 are inserted into syringe 101 the pressure inside the syringes immediately starts to build up. The insertion member for these pistons must be designed to not hinder the opening of the slits and still allow for passage of the escaping gas. As a result, this insertion member could be a hollow tube which fits around the slits and which provides for the air passage. The external sealing surface 301, 302, 304, 401, 404, or 601, 604 of the pistons shown in FIGS. 3,4,6, can be similar to those previously designed.

For storage or for operation of the syringe, a second actuation member is inserted into the cavities, 206, 306 or 406. This second actuation member 710 FIG. 7 can be threaded into the pistons 201, 301, 401 or 601 or they can be inserted as a snug fit into the resilient material. When the second actuation member 710 is inserted into piston 201 it completely fills the cavity 206. As a result, the resilient wall 212 cannot collapse since there is no cavity to collapse into. When the second actuation member 710 is inserted into the piston 301, it also completely fills the cavity 306 thus preventing the flap of slit 313 from opening. When the second actuation member 710 is inserted into piston 401 it not only completely fills the cavity 406, it also distorts the duckbills 412 collapsing them against the inner end 408 preventing slit 413 from opening. As a result, since the bypass condition cannot be achieved when the second actuation member 710 is inserted into cavities 206, 306 or 406, the pistons 201, 301 or 401 can only function as pressurizing pistons when the second actuation member is inserted into the respective cavities. It is obvious that the first actuation member can be designed so that when it is inserted into the cavity it allows the previously described to occur, and by rotating the actuation member, a blocking portion on the actuation member can rotate to prevent the wall 212 from collapsing and prevent the slit 313 and 413 from opening.

In some applications it may be desirable when using the piston 201 of FIG. 2 to have a lower complete sealing surface 204. As shown in FIG. 6, the inside of cavity 606 can be designed with a built up inner surface 614. This built up inner surface 614 is located inside the cavity at the same position where the lower sealing ring 604 is removed to provide the wall 612 and tapered surface 607. This built up inner surface will not effect the bypass function. When the second actuation member 710 is inserted or threaded into place it stretches the resilient material and expands the outer surface of the sealing ring 704 so that it makes a complete sealing ring against the surface 105 of syringe 101.

From the forgoing, it is seen that the present invention provides a syringe piston that can be inserted into a syringe without the use of added parts or equipment to allow the gas to escape while the piston is being inserted into the syringe with a first actuation member and it can still be used after insertion to pressurize the syringe when using a second actuation member to operate the syringe in a normal fashion.

What is claimed is:

1. A chamber with contents comprising a chamber open end, a chamber bottom, and a chamber side wall between said chamber bottom and said chamber open end, a resilient pressurizing piston for allowing expulsion of gas from said chamber and for applying pressure on said contents comprising; an outer portion on said piston, a inner portion on said piston facing said contents, and a piston wall on said piston extending from said inner portion to said outer portion, an outer surface of said piston wall adjacent said chamber side wall, an inner surface of said piston wall extending from said inner portion to said outer portion, a piston cavity formed by said inner surface and said inner portion, a first actuation means smaller than said cavity and separate of said piston for moving said piston into said chamber to generate gas pressure, said piston distortable at a predetermined pressure, said gas pressure distorting said piston when said gas pressure reaches said predetermined pressure to allow said gas pressure created by the movement of said piston in said chamber to escape during said piston's movement from said chamber open end towards said contents, and a second actuation means separate of said piston and of a size and configuration to fit within the cavity of the piston preventing said piston's distortion thus pressurizing said chamber when said piston is moved further toward said chamber bottom.

2. The chamber with contents according to claim 1 wherein said chamber bottom has an opening to allow exiting of said contents when said piston pressurizes said chamber.

3. The chamber with contents according to claim 1 wherein said outer portion of said piston is greater than said inner portion of said piston, said piston wall tapering from said inner portion to said outer end of said piston, said piston wall collapsible by said gas pressure into said cavity when said first actuation means moves said piston towards said contents, and said wall is prevented from collapsing when said second actuation means is inserted into said cavity.

4. The chamber with contents according to claim 1 wherein said resilient pressurizing piston includes an internal thread formed in said cavity that mates with an external thread on said second actuation means to thread said second actuation means formed into said cavity to fill said cavity to permit pressurization of said syringe.

5. The chamber with contents according to claim 1 wherein said first actuation means and said second actuation means consists of a single member rotatable to allow for the distortion of said piston in one position of rotation and for preventing the distortion of said piston in another position of rotation.

6. A resilient material piston capable of distorting during movement by a first actuation member in a given direction into a chamber and nondistortable during movement by a second actuation member in said given direction into the chamber, said piston comprising an inner end, an outer end, a wall between said inner end and said outer end, said wall comprising an outer surface and an inner surface, said outer surface at said inner end defining a first given area and said outer surface at said outer end defining a second given area greater than said first given area, said outer surface tapering from said first area to said second area, a cavity defined by said inner surface of said wall and said inner end, said cavity larger than said first actuation member and equal to or smaller than said second actuation member, a chamber into which said piston is inserted inner end first, said wall collapsible during insertion of said piston with said first actuation member and rigid during insertion with said second actuation member supporting said piston to prevent collapse thereof.

7. The resilient material piston according to claim 6 wherein said outer surface tapering from said first area to said second area occurs in more than one position.

8. The resilient material piston according to claim 6 wherein said outer surface tapering from said first area to said second area is continuous.

9. The resilient material piston according to claim 6 including a built up inner surface in said cavity to enable expansion of said inner end on insertion of said second actuating member.

10. The resilient material piston according to claim 6 including an outlet port in said chamber.

11. A resilient material piston for a chamber that can distort during a given movement in a given direction in a chamber by a first actuation means and is nondistortable during a given movement in said given direction in the chamber by a second actuation means, said piston comprising: an inner end, an outer end, a wall between said inner end and said outer end, said wall comprising an outer surface and an inner surface, a cavity defined by said inner surface and said inner end, said cavity larger than said first actuation means and equal to or smaller than said second actuation means, a normally closes slit in said inner end, said slit in said inner end openable when said piston is moved into said chamber by said first actuation means and said slit is restricted from opening when said piston is moved further into said chamber by said second actuation member.

12. The resilient material piston for a chamber according to claim 11 wherein said slit is a pair of flexible flaps held together by resilience of the material of said piston.

13. The resilient material piston for a chamber according to claim 11 wherein said first actuation means substantially surrounds said slit to allow for the pressurized gas to exit from said chamber during said given movement.

14. The resilient material piston for a chamber according to claim 11 wherein said chamber includes an outlet port.

15. The resilient material piston for a chamber according to claim 11 wherein said first actuation means and said second actuation means consist of a single member rotatable to achieve gas bypassing or pressurization.

* * * * *